United States Patent
Savage et al.

(10) Patent No.: US 10,456,508 B2
(45) Date of Patent: Oct. 29, 2019

(54) DRUG DELIVERY ENDOVASCULAR STENT AND METHOD OF USE

(71) Applicant: Biosensors International Group, Ltd., Hamilton (BM)

(72) Inventors: Douglas R. Savage, Del Mar, CA (US); John E. Shulze, Rancho Santa Margarita, CA (US); Ronald E. Betts, La Jolla, CA (US); Sepehr Fariabi, Newport Coast, CA (US); Shih-Horng Su, Irvine, CA (US)

(73) Assignee: Biosensors International Group, Ltd., Hamilton (BM)

( * ) Notice: Subject to any disclaimer, the term of this patent is extended or adjusted under 35 U.S.C. 154(b) by 261 days.

(21) Appl. No.: 15/406,475

(22) Filed: Jan. 13, 2017

(65) Prior Publication Data

US 2017/0128635 A1 May 11, 2017

Related U.S. Application Data

(63) Continuation of application No. 13/554,296, filed on Jul. 20, 2012, now Pat. No. 9,579,424, which is a
(Continued)

(51) Int. Cl.
*A61L 31/16* (2006.01)
*A61F 2/91* (2013.01)
(Continued)

(52) U.S. Cl.
CPC ............ *A61L 31/16* (2013.01); *A61F 2/91* (2013.01); *A61F 2/915* (2013.01); *A61L 31/022* (2013.01);
(Continued)

(58) Field of Classification Search
CPC .................................... A61F 2/82; B05D 3/00
See application file for complete search history.

(56) References Cited

U.S. PATENT DOCUMENTS 3,929,992 A 12/1975 Sehgal et al.
4,316,885 A 2/1982 Rakhit
(Continued)

FOREIGN PATENT DOCUMENTS

CN 101600463 B 1/2015
EP 0875218 A2 11/1998
(Continued)

OTHER PUBLICATIONS

Denny et al., Potential antitumor agents. 27. Quantitative structure—antileukemic (L 1210) activity relationships for the omega-(4-(9-acridinylamino)phenyl)alkanoic acids, Journal of Medicinal Chemistry, vol. 21, No. 5, 1990, pp. 2190-2200.
(Continued)

*Primary Examiner* — Dah-Wei D. Yuan
*Assistant Examiner* — Andrew J Bowman
(74) *Attorney, Agent, or Firm* — Kilpatrick Townsend & Stockton

(57) ABSTRACT

An improvement in drug-eluting stents, and method of their making, are disclosed. The surface of a metal stent is roughened to have a surface roughness of at least about 20 μin (0.5 μm) and a surface roughness range of between about 300-700 μin (7.5-17.5 μm). The roughened stent surface is covered with a polymer-free coating of a limus drug, to a coating thickness greater than the range of surface roughness of the roughened stent surface.

9 Claims, 14 Drawing Sheets

Related U.S. Application Data continuation of application No. 11/751,268, filed on May 21, 2007, now abandoned, which is a continuation-in-part of application No. 11/690,768, filed on Mar. 23, 2007, now Pat. No. 8,067,055.

(60) Provisional application No. 60/853,077, filed on Oct. 20, 2006.

(51) Int. Cl.
  A61F 2/915 (2013.01)
  A61L 31/02 (2006.01)
  A61L 31/10 (2006.01)
  A61F 2/848 (2013.01)
  A61F 2/82 (2013.01)
  A61F 2/89 (2013.01)

(52) U.S. Cl.
  CPC ............... *A61L 31/10* (2013.01); *A61F 2/82* (2013.01); *A61F 2/848* (2013.01); *A61F 2/89* (2013.01); *A61F 2002/825* (2013.01); *A61F 2002/91541* (2013.01); *A61F 2002/91566* (2013.01); *A61F 2210/0004* (2013.01); *A61F 2210/0014* (2013.01); *A61F 2220/0025* (2013.01); *A61F 2230/0013* (2013.01); *A61F 2240/001* (2013.01); *A61F 2250/0023* (2013.01); *A61F 2250/0025* (2013.01); *A61F 2250/0026* (2013.01); *A61F 2250/0036* (2013.01); *A61F 2250/0037* (2013.01); *A61F 2250/0051* (2013.01); *A61F 2250/0067* (2013.01); *A61F 2250/0068* (2013.01); *A61F 2250/0096* (2013.01); *A61L 2300/416* (2013.01); *A61L 2300/606* (2013.01); *A61L 2420/02* (2013.01)

(56) References Cited

U.S. PATENT DOCUMENTS

| | | |
|---|---|---|
| 4,650,803 A | 3/1987 | Stella et al. |
| 4,885,171 A | 12/1989 | Surendra et al. |
| 4,990,155 A | 2/1991 | Wilkoff |
| 5,100,899 A | 3/1992 | Calne |
| 5,120,842 A | 6/1992 | Failli et al. |
| 5,151,413 A | 9/1992 | Caufield et al. |
| 5,163,952 A | 11/1992 | Froix |
| 5,258,020 A | 11/1993 | Froix |
| 5,258,389 A | 11/1993 | Goulet et al. |
| 5,306,286 A | 4/1994 | Stack et al. |
| 5,288,711 A | 5/1994 | Mitchell et al. |
| 5,342,348 A | 8/1994 | Kaplan |
| 5,362,718 A | 11/1994 | Skotnicki et al. |
| 5,441,515 A | 8/1995 | Khosravi et al. |
| 5,464,650 A | 11/1995 | Berg et al. |
| 5,516,781 A | 5/1996 | Morris et al. |
| 5,527,337 A | 6/1996 | Stack et al. |
| 5,607,467 A | 3/1997 | Froix |
| 5,609,629 A | 3/1997 | Fearnot et al. |
| 5,649,977 A | 7/1997 | Campbell |
| 5,665,772 A | 9/1997 | Cottens et al. |
| 5,707,385 A | 1/1998 | Williams |
| 5,713,949 A | 2/1998 | Jayaraman |
| 5,716,981 A | 2/1998 | Hunter et al. |
| 5,733,327 A | 3/1998 | Igaki et al. |
| 5,735,872 A | 4/1998 | Carpenter et al. |
| 5,769,884 A | 6/1998 | Solovay |
| 5,824,048 A | 10/1998 | Tuch |
| 5,843,172 A | 12/1998 | Yan |
| 5,860,999 A | 1/1999 | Schnepp-pesch et al. |
| 5,873,904 A | 2/1999 | Ragheb et al. |
| 5,895,407 A | 4/1999 | Jayaraman |
| 5,902,317 A | 5/1999 | Kleshinski et al. |
| 5,912,253 A | 6/1999 | Cottens et al. |
| 5,922,393 A | 7/1999 | Jayaraman |
| 5,972,027 A | 10/1999 | Johnson |
| 6,013,853 A | 1/2000 | Athanasiou et al. |
| 6,019,784 A | 2/2000 | Hines |
| 6,022,371 A | 2/2000 | Killion |
| 6,042,606 A | 3/2000 | Frantzen |
| 6,053,939 A | 4/2000 | Okuda et al. |
| 6,080,177 A | 6/2000 | Igaki et al. |
| 6,096,175 A | 8/2000 | Roth |
| 6,099,562 A | 8/2000 | Ding et al. |
| 6,129,755 A | 10/2000 | Mathis et al. |
| 6,153,252 A | 11/2000 | Hossainy et al. |
| 6,156,062 A | 12/2000 | McGuinness |
| 6,174,329 B1 | 1/2001 | Callol et al. |
| 6,190,406 B1 | 2/2001 | Duerig et al. |
| 6,197,013 B1 | 3/2001 | Reed et al. |
| 6,231,600 B1 | 5/2001 | Zhong |
| 6,248,129 B1 | 6/2001 | Froix |
| 6,273,913 B1 | 8/2001 | Wright et al. |
| 6,299,604 B1 | 10/2001 | Ragheb et al. |
| 6,368,346 B1 | 4/2002 | Jadhav |
| 6,368,658 B1 | 4/2002 | Schwarz et al. |
| 6,384,046 B1 | 5/2002 | Schuler et al. |
| 6,527,919 B1 | 3/2003 | Roth |
| 6,540,777 B2 | 4/2003 | Stenzel |
| 6,585,151 B1 | 7/2003 | Ghosh |
| 6,585,764 B2 | 7/2003 | Wright et al. |
| 6,607,598 B2 | 8/2003 | Schwarz et al. |
| 6,623,521 B2 | 9/2003 | Steinke et al. |
| 6,641,611 B2 | 11/2003 | Jayaraman |
| 6,663,881 B2 | 12/2003 | Kunz et al. |
| 6,670,398 B2 | 12/2003 | Edwards et al. |
| 6,676,701 B2 | 1/2004 | Rourke et al. |
| 6,682,553 B1 | 1/2004 | Webler, Jr. |
| 6,730,064 B2 | 5/2004 | Ragheb et al. |
| 6,739,831 B2 | 5/2004 | Hsu et al. |
| 6,743,463 B2 | 6/2004 | Weber et al. |
| 6,746,773 B2 | 6/2004 | Llanos et al. |
| 6,774,278 B1 | 8/2004 | Ragheb et al. |
| 6,790,228 B2 | 9/2004 | Hossainy et al. |
| 6,805,898 B1 * | 10/2004 | Wu ............... A61F 2/0077 216/10 |
| 6,904,658 B2 | 6/2005 | Hines |
| 6,911,100 B1 | 6/2005 | Gibbs et al. |
| 6,913,617 B1 | 7/2005 | Reiss |
| 6,939,376 B2 | 9/2005 | Shulze et al. |
| 7,055,237 B2 | 6/2006 | Thomas |
| 7,128,755 B2 | 10/2006 | Su et al. |
| 7,344,563 B2 | 3/2008 | Vallana et al. |
| 7,537,610 B2 | 5/2009 | Reiss |
| 7,607,208 B2 | 10/2009 | Curcio et al. |
| 8,067,055 B2 | 11/2011 | Savage et al. |
| 9,579,424 B2 | 2/2017 | Savage et al. |
| 2001/0020151 A1 | 9/2001 | Reed et al. |
| 2001/0027340 A1 | 10/2001 | Wright et al. |
| 2001/0029351 A1 | 10/2001 | Falotico et al. |
| 2002/0005600 A1 | 1/2002 | Ma |
| 2002/0038146 A1 | 3/2002 | Harry |
| 2002/0051730 A1 | 5/2002 | Bodnar et al. |
| 2002/0082679 A1 | 6/2002 | Sirhan et al. |
| 2002/0098278 A1 | 7/2002 | Bates et al. |
| 2002/0111590 A1 | 8/2002 | Davila et al. |
| 2002/0111671 A1 | 8/2002 | Stenzel |
| 2002/0156022 A1 | 10/2002 | Edwards et al. |
| 2003/0033007 A1 | 2/2003 | Sirhan et al. |
| 2003/0050687 A1 | 3/2003 | Schwade et al. |
| 2003/0050692 A1 | 3/2003 | Sirhan et al. |
| 2003/0059454 A1 | 3/2003 | Barry et al. |
| 2003/0068355 A1 | 4/2003 | Shanley et al. |
| 2003/0077310 A1 | 4/2003 | Pathak et al. |
| 2003/0083646 A1 | 5/2003 | Sirhan et al. |
| 2003/0139801 A1 | 7/2003 | Sirhan et al. |
| 2003/0159920 A1 | 8/2003 | Roth |
| 2003/0225450 A1 | 12/2003 | Shulze et al. |
| 2004/0010002 A1 | 1/2004 | Wasik et al. |
| 2004/0024450 A1 | 2/2004 | Shulze et al. |
| 2004/0030380 A1 | 2/2004 | Shulze et al. |
| 2004/0073284 A1 | 4/2004 | Bates et al. |
| 2004/0249442 A1 | 12/2004 | James, III et al. |

(56) References Cited

U.S. PATENT DOCUMENTS

| | | |
|---|---|---|
| 2005/0038505 A1 | 2/2005 | Shulze et al. |
| 2005/0074545 A1 | 4/2005 | Thomas |
| 2005/0101624 A1 | 5/2005 | Betts et al. |
| 2005/0271701 A1 | 12/2005 | Cottone, Jr. et al. |
| 2006/0036316 A1 | 2/2006 | Zeltinger et al. |
| 2006/0069427 A1 | 3/2006 | Savage et al. |
| 2006/0155361 A1 | 7/2006 | Schomig et al. |
| 2006/0229711 A1 | 10/2006 | Yan et al. |
| 2008/0051868 A1 | 2/2008 | Cottone et al. |
| 2008/0051873 A1 | 2/2008 | Cottone et al. |
| 2008/0051874 A1 | 2/2008 | Cottone et al. |
| 2008/0051875 A1 | 2/2008 | Cottone et al. |
| 2008/0097575 A1 | 4/2008 | Cottone |

FOREIGN PATENT DOCUMENTS

| | | |
|---|---|---|
| EP | 0950386 A2 | 10/1999 |
| EP | 0970711 A2 | 1/2000 |
| JP | 10192413 A | 7/1998 |
| WO | 1997035575 A1 | 10/1997 |
| WO | 1998036784 A1 | 8/1998 |
| WO | 1999007308 A1 | 2/1999 |
| WO | 2001014387 A1 | 3/2001 |
| WO | 2001045763 A1 | 6/2001 |
| WO | 2002026162 A2 | 4/2002 |
| WO | 2002026281 A1 | 4/2002 |
| WO | 2002032347 A2 | 4/2002 |
| WO | 2002056790 A2 | 7/2002 |
| WO | 2003026718 A1 | 4/2003 |
| WO | 2006020742 A2 | 2/2006 |
| WO | 2006036801 A2 | 4/2006 |

OTHER PUBLICATIONS

Dibra et al., Influence of Stent Surface Topography on the Outcomes of Patents Undergoing Coronary Stenting: A Randomized Double-Blind Controlled Trial, Catherization and Cardiovascular Interventions, Catherization and Cardiovascular Interventions, vol. 65, 2005, pp. 374-380.

Ichihashi et al., A quantitative concept of the mechanism of intestinal lymphatic transfer of lipophilic molecules, Pharmaceutical Research, vol. 11, No. 4, 1994, pp. 508-512.

Japanese Application No. 2009-533384, Office Action dated Feb. 28, 2012, 8 pages. (5 pages of English translation and 3 pages of original document).

International Application No. PCT/US2007/022284 International Search Report dated Apr. 23, 2008, 4 pages.

Schwartz et al., Restenosis after balloon angioplasty. A practical proliferative model in porcine coronary arteries, Circulation, vol. 82, No. 6, Dec. 1, 1990, pp. 2190-2200.

Su et al., Expandable Bioresorbable Endovascular Stent. I. Fabrication and Properties, Annals of Biomedical Engineering, vol. 31, 2003, pp. 667-677.

* cited by examiner

DRUG DELIVERY ENDOVASCULAR STENT AND METHOD OF USE

CROSS-REFERENCE TO RELATED APPLICATIONS

This application claims the benefit of priority to U.S. Provisional Application No. 60/853,077, filed Oct. 20, 2006, and U.S. patent application Ser. No. 11/751,268, filed May 21, 2007, both of which are incorporated herein by reference in their entirety.

TECHNICAL FIELD

The present application relates to an endovascular stent at least partly including a textured or abraded surface, and a method of making and using the stent.

BACKGROUND

Complications such as restenosis are a recurring problem in patients who have received artherosclerosis therapy in the form of medical procedures such as percutaneous translumenal coronary angioplasty (PTCA). Restenosis is commonly treated by a procedure known as stenting, where a medical device is surgically implanted in the affected artery to prevent it from occluding post procedure.

A stent is typically cylindrical in shape and is usually made from a biocompatible metal, such as cobalt chromium or surgical steel. Most stents are collapsible and are delivered to the occluded artery via a translumenal catheter. The stent is affixed to the catheter and can be either self expanding or expanded by inflation of a balloon inside the stent that is then removed with the catheter once the stent is in place.

Complications that can arise from stent therapy include restenosis and thrombosis. In an effort to overcome these complications, stents may contain a layer or coating of an anti-restenosis drug that is released in a controlled fashion at the stent-implantation site. Typically, the drug is contained in a permanent or bioerodable polymer carrier, as disclosed, for example, in U.S. Pat. No. 5,716,981 issued to Hunter entitled "Anti-angiogenic Compositions and Methods of Use." Examples of typical therapies that are proposed to be delivered in this manner are antiproliferatives, anticoagulants, anti-inflammatory agents and immunosuppressive agents, although there are many other chemical and biological agents also mentioned in the patent literature. It has been suggested that the polymer carrier with drug may be covered by a porous biodegradable layer that serves to regulate controlled release of the drug into the body, as disclosed for example, in U.S. Pat. Nos. 6,774,278 and 6,730,064.

More recently, stents in which an anti-restenosis drug is carried in channels, grooves or pores for release in "polymer-free" i.e. pure-drug form have been proposed. Alternatively, stents having roughened surface intended to anchor a drug layer on the surface of the stent, for release in pure-drug form have been proposed, for example, in U.S. Pat. Nos. 6,805,898 and 6,918,927. None of these patents show or suggest that with particular classes of anti-restenosis compounds, it is possible to enhance the anti-restenosis activity of the compounds by selection of surface roughness features within certain ranges on the stent surface.

In light of the complications associated with stent therapy, it would be desirable to develop a stent having at least one roughened or textured surface for increased surface area, which can be manufactured in such a way as to maximize structural integrity, drug loading capacity, and ability to deliver drug to the vessel wall in a therapeutically enhanced way, as evidenced by a reduced risk of rate of occurrence or extent of restenosis following stent placement at the site of vascular injury.

SUMMARY

The invention includes, in one embodiment, an improvement in a method for reducing the rate of occurrence and/or extent of restenosis or thrombosis resulting from vascular injury in a subject, relative to that observed by placing at the site of injury, a smooth-surfaced expandable stent formed of interconnected metal filaments, by coating the outer surface of the stent filaments with a polymer carrier containing a limus drug. The improvement, which is intended to maintain or further reduce the rate of occurrence and/or extent of restenosis or thrombosis, relative to that achieved with a polymer-coated, limus-eluting stent, but without the presence of a polymer carrier, includes the steps of:

(a) roughening outer surface regions of the stent filaments to a surface roughness of at least about 20 µin (0.5 µm), and a surface roughness range (maximum peak-to-valley) of between about 300-700 µin (7.5-17.5 µm), and (b) coating the roughened regions of the stent filaments with a polymer-free coating of the limus drug, to a coating thickness greater than the surface roughness range of the roughened stent surface, that is, to a thickness that covers the roughened surface.

The stent filaments may be roughened to have a surface roughness of between about 20-40 µin (0.5 to 1 µm), and/or a surface roughness range of between about 300-500 µin (7.5-12.5 µm).

The surface roughening may be carried out by abrading the outer surface regions of the stent filaments with a pressurized stream of abrasive particles, by forming a hydrocarbon-film mask over outer surface regions of the stent filaments, selectively removing stent material exposed by the mask, and removing the mask, by laser etching the outer surface regions of the stent filaments, or by peening the outer surface regions of the filaments to imprint a pattern thereon.

The drug coating may be applied as a viscous solution of the drug onto the outer surfaces of the stent filament, with drying to form a solid drug coating on the stent filaments. The coating may be applied to a final amount of limus drug on the stent between 25 to 240 ug/cm stent length, and to a final coating thickness between 5 and 15 µm. One preferred class of limus drugs are the 42-0-alkoxyalkyl limus compounds, as exemplified by the 42-O-ethoxyethyl compound referred to herein as Biolimus A9™.

In another aspect, the invention includes an improvement in a method for administering an anti-restenosis drug from an expandable stent formed of interconnected metal filaments, by coating the outer surface of the stent with a polymer-free limus drug coating. The improvement, which is intended to reduce the rate of occurrence and/or extent of restenosis or thrombosis achieved with the polymer-free limus drug coating, comprises roughening the outer surface regions of the stent filaments which are coated by the limus drug, to a surface roughness of at least about 20 µin (0.5 µm), and a surface roughness range of between about 300-700 µin (7.5-17.5 µm).

Also disclosed is an expandable stent for use in reducing the rate of occurrence and/or extent of restenosis or thrombosis resulting when the stent is placed at a site of vascular injury. The stent includes an expandable stent body formed of interconnected metal filaments, and formed on outer surface regions of the stent filaments, a roughened surface characterized by a surface roughness of at least about 20 μin (0.5 μm), and a surface roughness range of between about 300-700 μin (7.5-17.5 μm), and carried on the roughened regions of the stent filaments, a polymer-free coating of the limus drug having a coating thickness greater than the range of surface roughness of the roughened stent surface.

These and other aspects and embodiments of the present invention will become better apparent in view of the detailed description in conjunction with the accompanying drawings.

DETAILED DESCRIPTION

I. Definitions

Unless indicated otherwise, the terms below have the following meanings herein.

"Surface roughness" or "roughness average" or "Ra" is the arithmetic average of absolute values of the measured profile height deviations taken within the sampling length or area measured from the graphical centerline or centerplane (the mean line or plane). It is measured typically by a non-contact surface optical profilometer, as discussed below, but may also be measured by a contact profilometer or by estimating peak and valley heights from a surface micrograph.

"Surface roughness range" or "Rt" is the maximum peak-to-valley distance, calculated as the sum of the maximum peak and maximum valley measurements of roughness with respect to a centerline or centerplane. It is typically measured by non-contact surface optical profilometer, but can also be measured by the other methods noted above.

"Limus drug" refers to a macrocyclic triene immunosuppressive compound having the general structure shown, for example, in U.S. Pat. Nos. 4,650,803, 5,288,711, 5,516,781, 5,665,772 and 6,153,252, in PCT Publication No. WO 97/35575, in U.S. Pat. No. 6,273,913B1, and in U.S. Patent Application/Publication Nos. 60/176,086, 2000/021217A1, and 2001/002935A1.

"42-O-alkoxyalkyl limus drug" refers to the 42-O alkoxyalkyl derivative of rapamycin described in U.S. patent application publication no. 20050101624, published May 12, 2005, which is incorporated herein in its entirety. For example, "42-O-alkoxyalkyl limus drug" is "42-O-ethoxyethyl rapamycin," also referred to herein as "Biolimus A9."

"Polymer-free coating" means a coating whose structure and cohesiveness are provided by the drug itself, with or without the presence of one or more binding agents, rather than by a polymer matrix in which the drug is embedded, i.e., a polymer carrier.

II. Endovascular Stent

Figure 1:
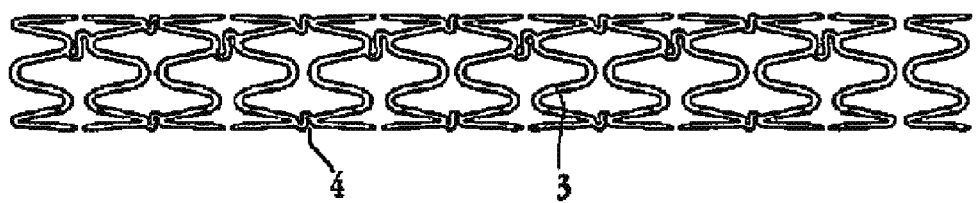
FIG. 1 is a scanned image of an endovascular stent having a metal filament body.

FIG. 1 shows a stent constructed in accordance with the invention, in the stent's contracted state. The stent includes a structural member or body with at least one surface being at least partly roughened or abraded at least for holding and releasing an anti-restenosis compound, as will be described further below.

In the embodiment shown, the stent body is formed of a series of tubular members called struts 3 connected to each other by filaments called linkers 4. Each strut 3 has an expandable zig-zag, sawtooth, helical ribbon coil or sinusoidal wave structure, and the connections to each linker 4 serve to increase overall stent flexibility. The contracted-state diameter of the stent is between approximately 0.5 mm-2.0 mm, preferably 0.71 to 1.65 mm, and a length of between 5-100 mm. The expanded stent diameter is at least twice and up to 8-9 times that of the stent in its contracted state, for example, a stent with a contracted diameter of between 0.7 to 1.5 mm may expand radially to a selected expanded state of between 2.0-8.0 mm or more. Stents having this general stent-body architecture of linked, expandable tubular members are known, for example, as described in PCT Publication No. WO 99/07308, which is commonly owned with the present application and expressly incorporated by reference herein.

Preferably, the stent structure is made of a biocompatible material, such as stainless steel. Further examples of biocompatible materials that are typically used for the stent structure are, cobalt chromium, nickel, magnesium, tantalum, titanium, nitinol, gold, platinum, inconel, iridium, silver, tungsten, or another biocompatible metal, or alloys of any of these; carbon or carbon fiber; cellulose acetate, cellulose nitrate, silicone, polyethylene teraphthalate, polyurethane, polyamide, polyester, polyorthoester, polyanhydride, polyether sulfone, polycarbonate, polypropylene, high molecular weight polyethylene, polytetrafluoroethylene, or another biocompatible polymeric material, or mixtures or copolymers of these; poly-L-lactic acid, poly-DL-lactic acid, polyglycolic acid or copolymers thereof, a polyanhydride, polycaprolactone, polyhydroxybutyrate valerate or another biodegradable polymer, or mixtures or copolymers of these; a protein, an extracellular matrix component, collagen, fibrin or another biologic agent; or a suitable mixture of any of these. An example of a typical stent is described in U.S. Pat. No. 6,730,064. The dimensions of each stent will vary depending on the body lumen in which they are to be delivered. For example, a stent may have a diameter ranging from approximately 0.5 mm to approximately 25.0 mm and a length that ranges from approximately 4 mm to approximately 100 mm or longer. An example of stent measurements is described in co-owned U.S. Pat. No. 6,939,376, which is commonly owned and expressly incorporated by reference herein.

Figure 2A:
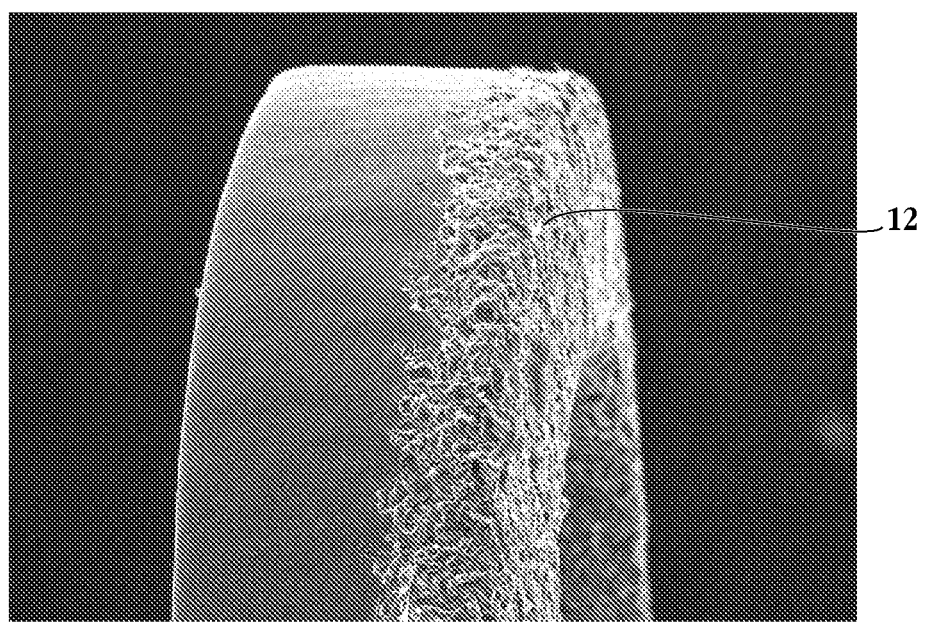
FIG. 2A is a scanning electron micrograph of an abraded stent surface.
Figure 2B:
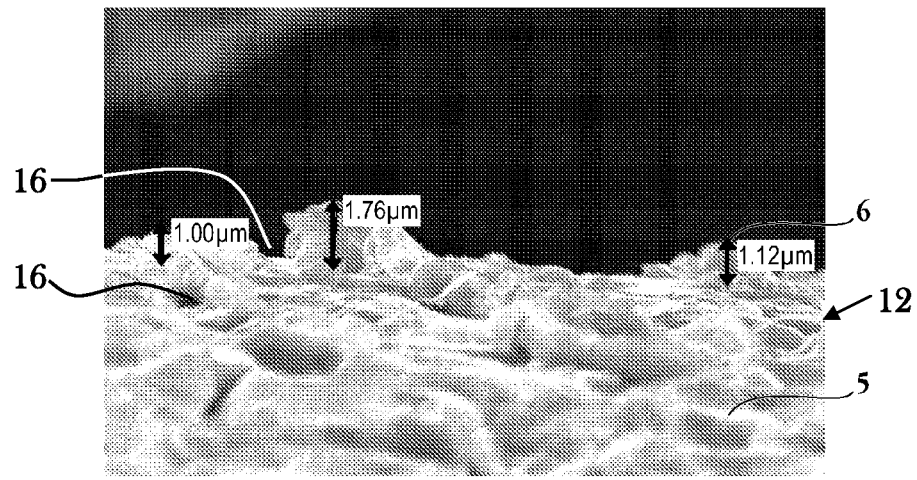
FIG. 2B is a scanning electron micrograph of the surface of FIG. 2A showing quantification of peaks generated on the stent surface after abrasion.
Figure 2C:
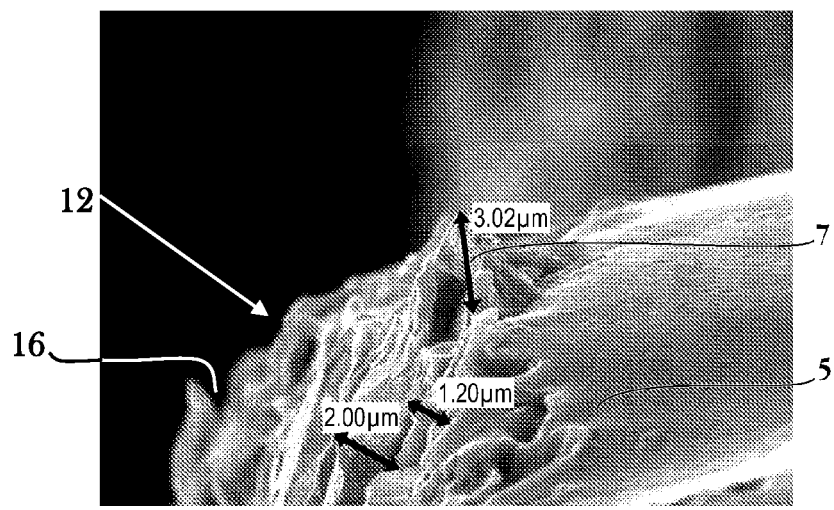
FIG. 2C is a scanning electron micrograph of the surface of FIG. 2A showing quantification of valleys generated on the stent surface after abrasion.

As seen in FIG. 2A, at least a portion of at least one of the surfaces of the stent has a roughened or abraded microstructure or textured surface 12. This microstructure can include at least one therapeutic agent that elutes from the microstructure. As seen in FIGS. 2B-2C, the roughened or textured surface 12 provides interstices or vertically projecting surface features and/or regions of undercuts or recesses 16. It will be appreciated that a solution containing a therapeutic agent can be drawn, e.g., by capillary forces into such recesses 16 and coat the projecting surfaces. In this manner, the surface area for coating the stent may be increased. The thickness of such layer refers to the average thickness of the layer, e.g., average depth of the infusible portion of the layer. Preferably, and as seen in FIG. 2A, at least a portion of the abluminal surface of the stent, i.e., the surface in contact with the treated vessel after stent placement, includes the microstructure surfacing.

III. Methods of Preparing Textured Surface

In one embodiment, not shown, the method includes use of a mask to prevent at least a portion of the stent from being abraded. Preferably, the mask is a hydrocarbon film, such as PARAFILM®, however, it will be appreciated that any suitable barrier to abrasion is suitable for use in these methods. Accordingly, in a preferred embodiment, at least the lumenal surface of the stent is not abraded. In one embodiment, a sheet of the mask approximately 5 mm by 60 mm is rolled around the diameter of a mandrel such as a 1.4 mm glass capillary tube. The stent is positioned onto the mandrel and hand-crimped into the hydrocarbon mask. A stereo microscope set between 10× and 40× may be used to ensure that the portion of the stent that is not to be abraded is covered by the mask. In a preferred embodiment, at least 80% of the stent wall thickness on all surfaces is masked by the hydrocarbon film layer.

In one embodiment, the stent surface 5 is then treated by utilizing microblasting systems, not shown, such as the MICRO BLASTER® and PROCENTER® by Comco, Inc. or an equivalent. In one embodiment, 25 µm of an abrasive, such as aluminum oxide, is used to roughen the stent surface 5. The pressure is adjusted to 40 psi±5 psi, and a spray nozzle is positioned approximately 2.5 cm to 5.0 cm from the stent surface 5, making multiple passes over the stent.

In another embodiment, the mask is removed by any appropriate means such as via ultrasonic cleaning, not shown. Typically the ultrasonic cleaner is filled with deionized water which is heated to 45° C. A sample vial of HPLC grade chloroform is heated to between 50-60° C. on a hotplate. A glass capillary tube mandrel with a treated stent is incubated in a vial of 40° C. and 50° C. HPLC grade chloroform for 5-10 minutes. The vial containing the chloroform and mandrel is then sonicated in 45° C. deionized water for two minutes.

Due to the roughening of the stent surface 5, different elements are expressed on the metal surface, which can increase the susceptibility to corrosion. As a result, the treated stent is generally passivated according to ASTM standards and cleaned in a series of solvents such as Chloroform, Acetone and/or Isopropyl Alcohol. In one embodiment, after the mask is removed and the treated stent is sonicated, it is removed from the vial of chloroform. A sample vial is rinsed with Acetone and then refilled with Acetone. The treated stent is placed in the vial and sonicated in the ultrasonic cleaner for two minutes. The vial is rinsed with isopropyl alcohol and then refilled with isopropyl alcohol. The stent is sonicated in the ultrasonic cleaner for two more minutes. The treated stent is then passivated in a 60° C.±3° C. 20% by volume Nitric Acid bath for 30 minutes. The stent is then rinsed 10 times with copious amounts of deionized water. The stent is then placed in 600 mL of a solvent such as isopropyl alcohol and sonicated in the ultrasonic cleaner for 5 minutes and allowed to air dry.

In another embodiment, not shown, the surface 5 of the stent is uniformly abraded in a controlled manner via shot peening. Roughening of a stent surface 5 is accomplished using metal particles called shot that range in size from approximately 1 to 5 microns and is made from an atomic element having at least a weight of 43 g/mol. For example, the shot may be in the form of particulate tantalum, particulate tungsten, particulate platinum, particulate iridium, particulate gold, particulate bismuth, particulate barium, particulate zirconium and alloys thereof. Examples of suitable alloys include a platinum/nickel alloy and a platinum/iridium alloy.

In another embodiment, not shown, a stent surface 5 can be treated to create mechanical injectors that range in size from about 3 to about 10 microns.

In another embodiment, not shown, a stent surface 5 can be laser etched to create regular or irregular patterns of asperities/mechanical injectors of about 5 to about 25 microns.

In another embodiment, not shown, the stent surface 5 can be treated to have a different roughness factor on the ablumenal surface than the lumenal surface. For example the whole surface 5 may be treated via any of the above disclosed methods. Then a subsequent masking of the lumenal surface is performed so that a second surface treatment can be directed to the ablumenal surface. The subsequent treatment would typically utilize the more aggressive texturing process. The differing surfaces thus obtained can be used to impart differing useful properties to the inside (i.e. lumenal) vs. outside (ablumenal) surfaces of the stent. In one embodiment, the lumenal surface roughness is optimized to improve cell ingrowth and adhesion, for example as described in (US Patent Application No. 2005/0211680), and the ablumenal surface roughness may be optimized to provide drug transfer from the ablumenal surface of the stent to the surrounding tissues as described herein.

The stent surface 5 may be treated by placing desired amount of shot over a predetermined portion of the stent surface 5 and in the desired pattern. Pressure is applied to the particles using plates or rollers to make indentations in the stent surface 5. Roughness can also be achieved by jet blasting the particles at the stent surface 5 at a velocity sufficient to make indentations. An example of shot peening a metal surface is described in U.S. Pat. No. 6,911,100.

In a further embodiment, not shown, this uniform, controlled surface roughness can also be achieved similar to above by employing a laser rather than the use of shot. A series of electric discharges are applied to the desired portion of the outer or inner stent surface 5. The electric discharges contact the surface with sufficient energy to vaporize the material on the surface of the stent, creating pits, sometimes called voids, the combined effect of which is a rough surface having increased surface area. An example of this process is described in U.S. Pat. No. 6,913,617.

In another embodiment, not shown, the surface 5 of the stent is uniformly treated by compression. The stent is affixed to a mandrel, which is inserted into a die that is equipped with preformed raised portions that form indentations in the desired amount, shape, size and pattern on the stent surface 5. The indentations may be made in a number of ways such as welding them onto the stent surface 5 or sandblasting. The die is then closed around the stent forming indentations of the desired depth and covering the desired surface area. The stent is treated over its entire surface, or a portion of the surface, depending on the manufacture of the die. An example of this process is described in U.S. Pat. No. 7,055,237.

Figure 3A:
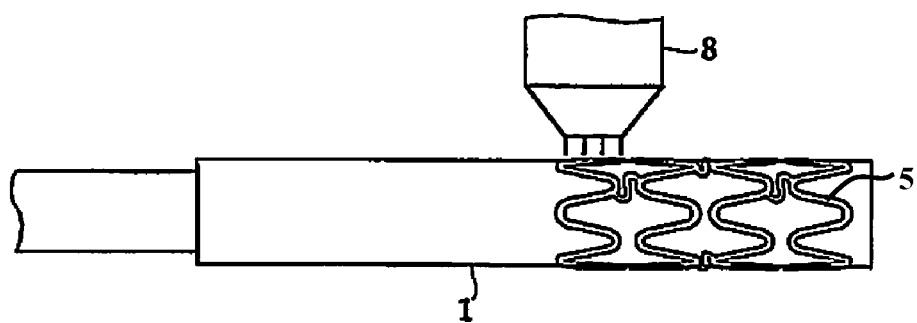
FIG. 3A is an illustration of a pneumatic press treating a stent surface.
Figure 3B:
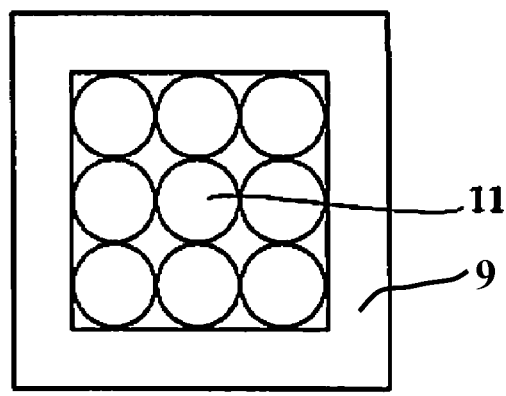
FIG. 3B is a close up frontal view of the fixed-head punch assembly of FIG. 3A showing the pneumatic press with multiple peeners.
Figure 3C:
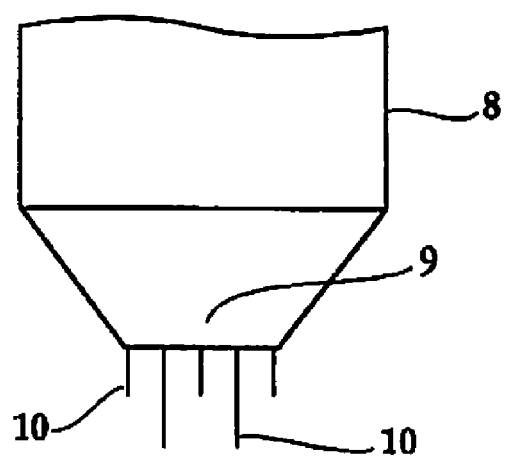
FIG. 3C is close up side view of the fixed head punch assembly of FIG. 3B.
Figure 3D:
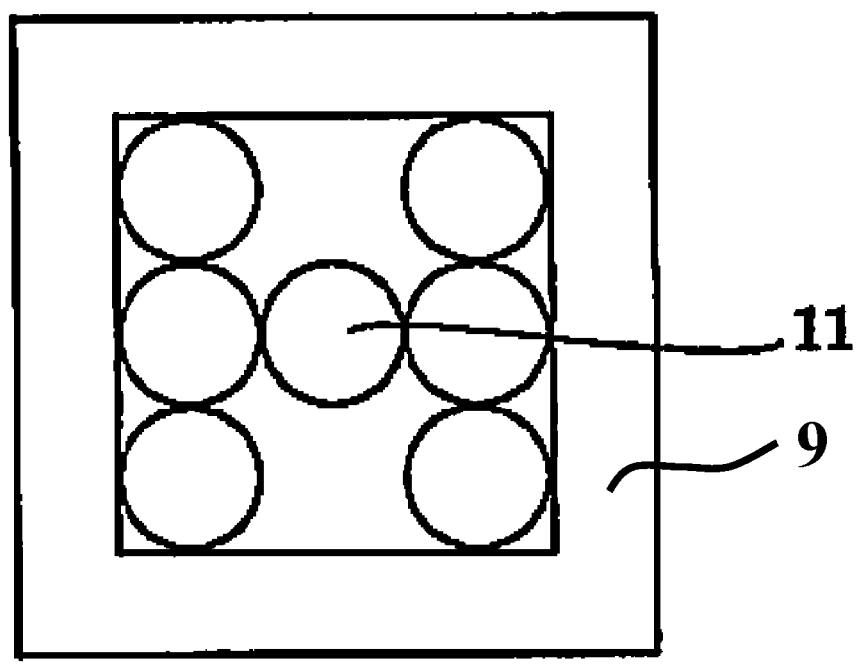
FIG. 3D is a close up frontal of the fixed-head attachment for the punch assembly of the pneumatic press of FIG. 3A showing an exemplary pattern.

In another embodiment, shown in FIGS. 3A and 3C, a stent surface 5 is treated with a pneumatic press or hydraulic press 8. Pneumatic presses are well known in the art as described in U.S. Pat. No. 4,079,617. Hydraulic presses are also well-known in the art as described in U.S. Pat. No. 7,033,155. As seen in FIG. 3A, the stent is positioned on a mandrel 1 that is either stationary or rotating. A computer controlled pneumatic or hydraulic press 8 is configured to treat the surface 5 of the stent in one of several predetermined ways, for example, randomly or in a desired pattern. Referring to FIGS. 3B-3D, the punch assembly 9 of the press may be configured to contain one or more peeners 10, 11, here defined as indentation creating mechanisms. In a preferred embodiment, the punch assembly contains a plurality of peeners 10, 11. It will be appreciated that the peeners 10, 11 may be of uniform or varied length in order to form the surface microstructure. Each peener 10, 11 remains in a retracted position until the computer is programmed to treat the stent surface 5. According to the selected program, the peeners 10, 11 will be depressed onto the stent surface 5 (not shown) with enough force to result in an indentation. Generally, the punch assembly 9 is configured to be no more than the width of the desired stent. For example, if the stent strut 3 (not shown) is 15 micron, the plurality of peeners 10, 11, will total no more than 15 micron on width as well. The number of peeners 10, 11 on a given punch assembly 9 will vary depending on the width of the stent. Similarly, the punch assembly 9 may be configured to be a preformed head affixed to the press wherein the heads are interchangeable depending on which pattern is desired. Also, the head can be stationary and the stent is turned or, in the alternative, the head can be moveable, this is embodied in a single peener 10, 11 affixed to the press that will randomly make impressions on the stent surface 5.

In another embodiment, not shown, the entire length of the tubing used to create stents, for example tubing that is 2.5 meters in length, is treated prior to laser cutting it into a plurality of desired stent lengths. The stent is horizontally or vertically attached to one or more mandrels 1 and abraded using one of the methods disclosed in this application. In terms of the abrading techniques, the stent is treated randomly, uniformly or in a desired pattern. Further, the length and sides of the stent is treated lengthwise, vertically or spirally. Moreover, the stent surface 5 is treated either by moving it over a stationary roughening mechanism, or in the alternative, the entire stent tube length is stationary and the roughening mechanism may be moved over the length of the tube in one of the manners disclosed, for example horizontally, vertically, spirally.

Potentiodynamic corrosion testing was performed on the treated stent to confirm the desirability of the passivation step and its effectiveness. The data shows that the treated, passivated stent breakdown potential is well within ASTM specified voltage levels standards. Therefore, after the roughening process and passivation, the treated stent does not exhibit a greater likelihood of corrosion when compared to the untreated control stent, and the roughening process does not increase the potential for restenosis and thrombosis. After passivation, the biocompatibility of the microstructured metal surface was observed to be equivalent to that observed with stents having smooth electropolished surfaces.

The approximate thickness of an untreated stent wall is generally around 0.05 mm. As seen in FIGS. 2B-2C, the treatment of the stent surface 5 in the manner disclosed results in a treated stent surface with a peak 6 height averaging approximately 1.30 μm and a valley 7 depth averaging 2.08 μm, respectively. To measure the effects, if any, that the roughening process has on the stent's structural integrity, axial fatigue testing and auger analysis were performed on a treated stent. Axial fatigue testing was focused at the portion of the stent that is the most susceptible to breakage, which is the link 4 between stent struts 3 (not shown). After over 3 million cycles in simulated physiological conditions, the untreated stent control and the roughed stent both remained intact. Since a portion of the treated stent is removed in the roughening process, and it has been discovered that the treated stent is able to withstand the same fatigue conditions as an untreated intact stent with more surface area is able to withstand, it is understood that the roughening process actually increases the fatigue resistance of the stent due to the disrupted microcrystalline structures of the stent body. Finally, auger analysis was performed on the treated stent to characterize the surface chemistry, which revealed similar ratios of identical elements in the passivated unroughened stent and the passivated roughened stent. This demonstrates that the process of passivating the treated stent in the manner disclosed has no deleterious effects on the surface chemistry of the stent.

Example 2 (further details of which are provided below) provides surface roughness Ra and roughness factor Rt measurements for four stents prepared as described above by surface abrasion with a pressurized particle blast. As seen, the surface roughness values were all at least 20 μin (0.5 μm) and are typically between about 20-40 μin (0.5 μm-1.0 μm), and a roughness range between 300-700 μin (7.5 to 17.5 μm), and typically between 300 and 500 μin (7.5 μm and 12.5 μm). In accordance with one aspect of the invention, these roughness values, and particularly the roughness range values, have been found optimal for achieving optimal anti-restenosis results in subjects.

Without wishing to be limited to a particular theory as to this effect, it appears that the surface asperities or projections in the 300-700 μin peak to valley range are optimal for "injecting" drug in the drug coating into the surrounding vessel. Thus, for example, as the projections are exposed, either by drug dissolution from the coating or by fractures in the coating during stent placement, the projections, by impacting or penetrating the local vessel area, may facilitate entry of the drug into the vessel. The result is that the defined roughness range of the stent surface, combined with the polymer-free drug coating, maintains or further reduces the rate of occurrence and/or extent of restenosis or thrombosis seen with a polymer-coated, limus-eluting stent, but without the presence of a polymer carrier, and further reduces the rate of occurrence and/or extent of restenosis or thrombosis seen with a polymer-free coating on a less-roughened surface, i.e., having a lower surface roughness range. Further, studies conducted in support of the present invention indicate that a stent having surface-roughness features with peak-to-height values in the range 800-1,000 μin (20-25 μm or more) may be less effective in reducing restenosis.

Thus, in one aspect, the invention is directed to improving the effectiveness, in terms of reduced incidence and/or extent of restenosis, in treating a vascular injury with a drug-eluting stent, e.g., a limus-eluting stent. The improvement includes the steps of roughening at least the ablumenal surface portions of the stent to a surface roughness of at least about 20 μin (0.5 μm), and a surface roughness range of between about 300-700 μin (7.5-17.5 μm), and coating the roughened regions of the stent filaments with a polymer-free coating of the limus drug, to a coating thickness greater than the range of surface roughness of the roughened stent surface, that is, to a coating thickness that forms a substantially unbroken drug coating.

Preferably, an API (i.e., active pharmaceutical ingredient) such as the antiproliferative Biolimus A9™ is applied at least to the ablumenal portion of the stent. The API may be applied to the stent surface by any appropriate means including by spraying the treated surface of the stent with a solution of the API. The API solution may also be applied by dipping the entire stent into the desired API or by applying it directly to the stent surface 5 manually. Biolimus A9™ has an amorphous to semi-crystalline structure that does not crack or fracture like some other crystalline limus compounds. Therefore, the properties of Biolimus A9™ permit adhesion to the stent's roughened treated surface in the unexpanded state and the expanded state.

Preferably, the API material is applied to the ablumenal portion of the stent via autopipetting, as described in co-owned U.S. Pat. No. 6,939,376. A solution ranging in a concentration of approximately 100 mg/ml to approximately 200 mg/ml is made by dissolving the desired API in an appropriate solvent, such as ethyl acetate or acetonitrile. The solution is placed in a reservoir with a pump designed to deliver the solution at a predetermined rate. The pump is controlled by a microcontroller, such as the 4-Axis Dispensing Robot Model available from I&J Fisnar Inc. A solution delivery tube for delivery of the solvent mixture to the stent surface 5 is attached to the bottom of the reservoir. The reservoir and delivery tube are mounted to a moveable support that moves the solvent delivery tube continuously or in small steps, for example, 0.2 mm per step along the longitudinal axis.

An uncoated stent is gripped by a rotating chuck contacting the inner surface of the stent at least at one end. Axial rotation of the stent is accomplished by rotating the stent continuously, or in small degree steps, such as 0.5 degree per step. Alternatively, the delivery tube is held at a fixed position and, in addition to the rotational movement, the stent is moved along its longitudinal direction to accomplish the coating process.

Prior to use, the solution delivery tubes are drawn and shaped under a Bunsen burner to form a small tapered opening at the tip of the tube to facilitate precise application of the drug/solvent mixture, which can then be applied over the length and sides of the stent as needed with the formed tip of the tube. It is within the scope of the invention to use more than one of the fluid dispensing tube types working in concert to form the coating, or alternately to use more than one moveable solution reservoir equipped with different tips, or containing different viscosity solutions or different chemical makeup of the multiple solutions in the same process to form the coating.

In another embodiment, not shown, a non-porous layer of parylene, parylene derivative, or another biocompatible polymer is applied to the treated stent surface, and the desired API is applied or layered onto that. Optionally, an additional layer of slightly non-porous polymer is applied directly over the API, which aids in controlled release over time. According to the present invention, the stent comprises at least one layer of an API posited on its surface, and the other surfaces will either contain no API or one or more different APIs. In this manner, one or more APIs may be delivered to the blood stream from the lumenal surface of the stent, while different treatments for different conditions are delivered on the vascular injury site/outside surface of the stent.

Figure 4:
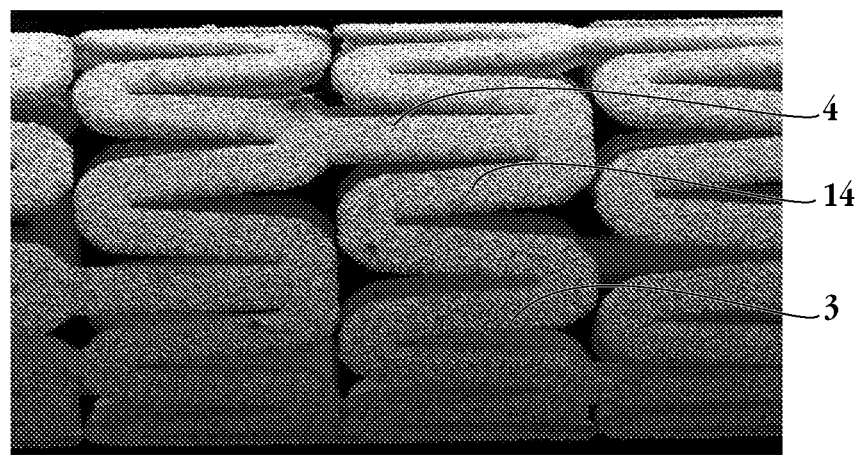
FIG. 4 is a scanning electron micrograph of a drug-coated, treated stent.

In another embodiment the stent is capable of being coated with an API molecule without the need of a polymer. As seen in FIG. 4, the process of roughening all or a portion of the stent in one of the methods disclosed above allows for the API to adhere directly to the surface of the treated stent 14. In one general embodiment, the API is a limus drug, such as described in U.S. Pat. Nos. 4,650,803, 5,288,711, 5,516, 781, 5,665,772 and 6,153,252, in PCT Publication No. WO 97/35575, in U.S. Pat. No. 6,273,913B1, and in U.S. Patent Application/Publication Nos. 60/176,086, 2000/021217A1, and 2001/002935A1. Exemplary limus drugs are the 42-O-alkoxyalkyl drugs, such as Biolimus A9™. Additional API drugs that may be employed, either alone, or in combination with a limus drug, include antiplatelet or antithrombotic agents, or anti-inflammatory agents such as dexamethasone, dexamethasone acetate, dexamethasone sodium phosphate, or another dexamethasone derivative or an anti-inflammatory steroid. Either the inside and/or outside surfaces of the stent can also be used to deliver other types of API molecules such as thrombolytics, vasodilators, antihypertensive agents, antimicrobials or antibiotics, antimitotics, antiproliferatives, antisecretory agents, non-steroidal anti-inflammatory drugs, immunosuppressive agents, growth factors and growth factor antagonists, antitumor and/or chemotherapeutic agents, antipolymerases, antiviral agents, photodynamic therapy agents, antibody targeted therapy agents, prodrugs, sex hormones, free radical scavengers, antioxidants, biologic agents, radiotherapeutic agents, radiopaque agents and radiolabelled agents.

The stent may be included in an assembly consisting of a stent body surrounding a deflated balloon affixed to the distal portion of a catheter which is used to implant the stent at the vascular injury site. The stent is introduced into the cardiovascular system of a patient via the brachial or femoral artery using the catheter. The catheter assembly is advanced through the coronary vasculature until the deflated balloon and stent combination is positioned across the vascular injury site or site of vascular disease or site of vascular narrowing. The balloon is then inflated to a predetermined size to expand the stent to a diameter large enough to be in continuous contact with the lumen. The balloon is then deflated to a smaller profile to allow the catheter to be withdrawn from the patient's vasculature, leaving the stent in place. An example of a typical stent implantation procedure is described in U.S. Pat. No. 6,913,617.

IV. Methods of Use

This section describes vascular treatment methods in accordance with the invention, and the performance characteristics of stents constructed in accordance with the invention.

The methods of the invention are designed to minimize the risk and/or extent of restenosis in a patient who has received localized vascular injury, or who is at risk of vascular occlusion due to the presence of advanced atherosclerotic disease. Typically the vascular injury is produced during an angiographic procedure to open a partially occluded vessel, such as a coronary or peripheral vascular artery. Alternately, the stent may be introduced into a site of vascular narrowing, and expanded using the balloon to directly open up the narrowed portion of the vessel (i.e. the vascular injury disease site). In the first mentioned angiographic procedure, a balloon catheter is first placed at the occlusion site, and a distal-end balloon is inflated and deflated one or more times to force the occluded vessel open. This vessel expansion, particularly involving surface trauma at the vessel wall where plaque may be dislodged, often produces enough localized injury that the vessel responds over time by cell proliferation and reocclusion in the vicinity of the implanted stent. Not surprisingly, the occurrence or severity of restenosis is often related to the extent of vessel stretching involved in the angioplasty procedure. Particularly where overstretching is 10% or more, restenosis occurs with high frequency and often with substantial severity, i.e., vascular occlusion. In the second mentioned alternative procedure of direct stent placement without prior angioplasty (i.e. "direct stenting") there is nevertheless still vascular injury induced by the expansion of the stent and balloon at the vascular injury disease site which results in restenosis and cellular proliferation at the site of the stent implantation, very similar in severity to that seen from the first mentioned procedure.

The present invention is intended to be used without limitations to any particular method of treating an injury at the vascular site, and can be used with either of the techniques described above, or with alternative techniques for vascular disease and injury as is known. In practicing the present invention, the stent is placed in its contracted state typically at the distal end of a catheter, either within the catheter lumen, or in a contracted state on a distal end balloon. The distal catheter end is then guided to the injury site, or to the site of potential occlusion, and released from the catheter, e.g., by pulling back a sheath covering the stent to release the stent into the site, if the stent is self-expanding, or by expanding the stent on a balloon by balloon inflation, until the stent contacts the vessel walls, in effect, implanting the stent into the tissue wall at the site.

Figure 5:
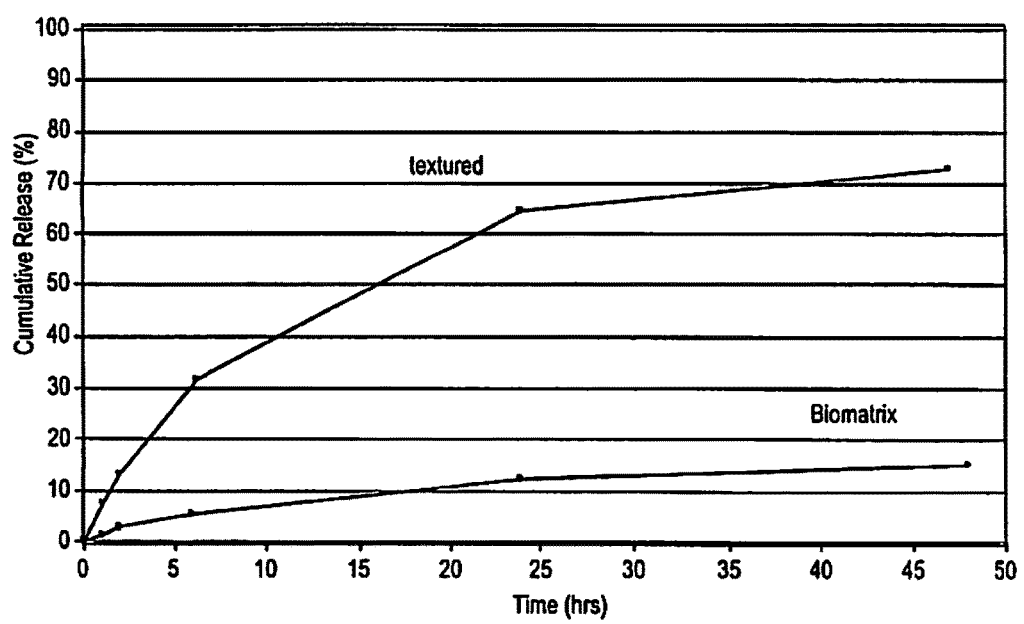
FIG. 5 is an elution profile of the drug Biolimus A9™ from the present stent and the Biomatrix® II stent as measured by the percentage of the total amount of drug released over cumulative time in hours.

Once deployed at the site, the drug coated stent begins to release active compound (API) into the cells lining the vascular site, to inhibit cellular proliferation and/or for other therapeutic benefits such as reduction of inflammation, limitation of thrombosis formation, reduction in cell apoptosis, etc. FIG. 5 shows Biolimus A9™ release kinetics from two stents, one with the drug coated onto a surface textured stent and the other a Biomatrix® II stent with a polymer coating containing Biolimus A9™.

Figure 6:
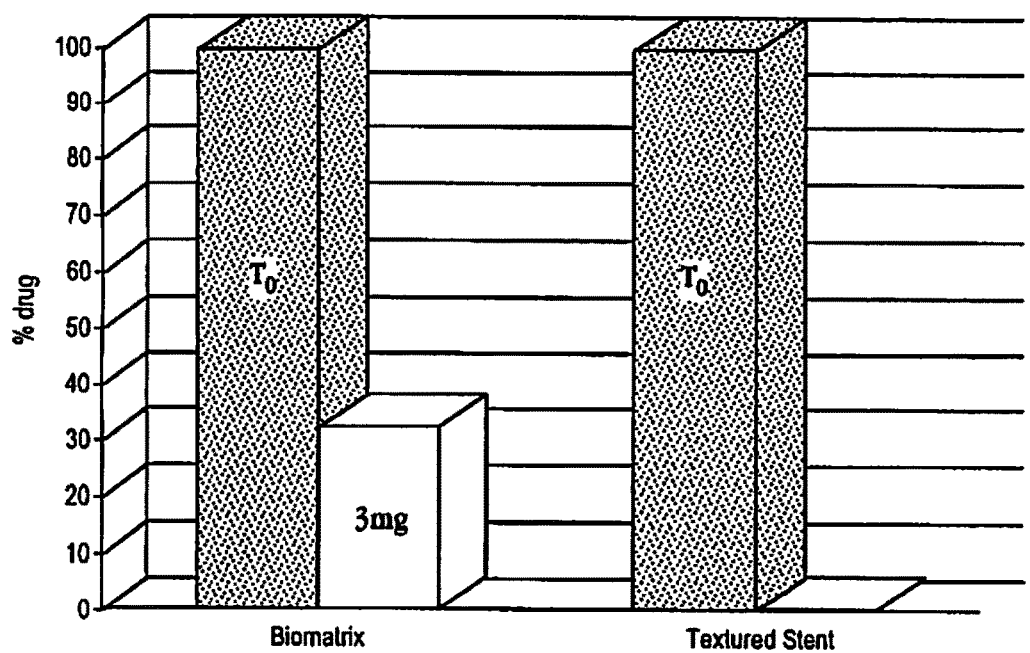
FIG. 6 is a graph showing the percentage of the drug Biolimus A9™ released from the present stent and a Biomatrix® II in a porcine implant model at three and two months, respectively.

FIG. 6 shows the percentage of drug release of Biolimus A9™ from a polymer coated stent (i.e., Biomatrix®) and a textured stent. As seen in the graph, after only two months, 100% of the Biolimus A9™ was released from the textured stent. In contrast, after three months, approximately 30% of the drug remained on the polymer coated stent.

Figure 7:
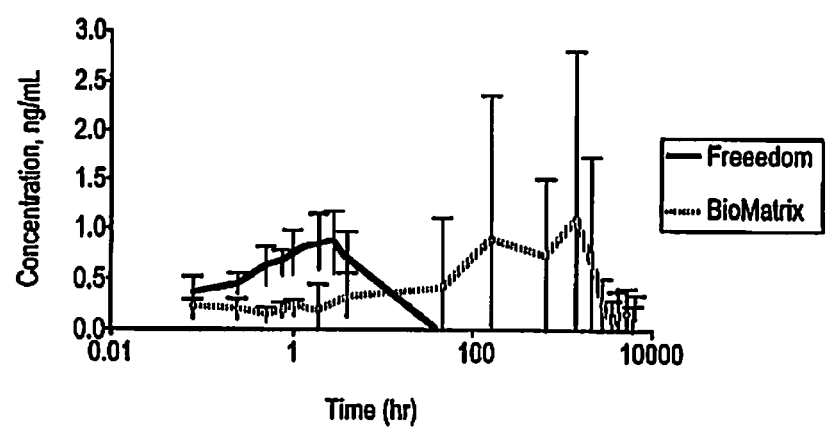
FIG. 7 is a graph showing the peak concentration in ng/mL of the drug Biolimus A9™ in peripheral blood over time in hours as released from the present stent and a Biomatrix® II stent in a porcine implant model as measured by mass spectroscopy.

FIG. 7 shows the peak blood concentration of Biolimus A9™ as measured by mass spectroscopy for each of the polymer coated Biomatrix® II and textured non-polymeric stent. As seen in the figure, the Biolimus A9™ blood concentration peaks at about four hours with the textured stent. The peak blood concentration of Biolimus A9™ with the polymer coated Biomatrix® II is at about two months.

FIGS. 9A-9F show in cross-section, a vascular region having an implanted bare metal stent (FIGS. 9A-9B), a metal Biomatrix® II stent having a polymer coating of 225 µg PLA and 225 µg Biolimus A9™ (FIGS. 9C-9D), and a textured stent with 225 µg Biolimus A9™ (FIGS. 9E-9F), where the coated filaments are seen in cross section. The figures illustrate the release of anti-restenosis compound from each filament region into the surrounding vascular wall region. Over time, the smooth muscle cells forming the vascular wall begin to grow into and through the lattice or helical openings in the stent, ultimately forming a continuous inner cell layer that engulfs the stent on both sides. If the stent implantation has been successful, the extent of late vascular occlusion at the site will be less than 50%, that is, the cross-sectional diameter of flow channel remaining inside the vessel will be at least 50% of expanded stent diameter at time of implant.

Trials in a porcine restenosis animal model as generally described by Schwartz et al. ("Restenosis After Balloon Angioplasty-A Practical Proliferative Model in Porcine Coronary Arteries", Circulation 82:(6) 2190-2200, December 1990.) Studies have been conducted in the porcine model which demonstrate the ability of the stent of this invention to limit the extent of restenosis, and the other advantages of the stent over currently proposed and tested stents. The studies are summarized in Example 3, explained in further detail below.

Briefly, the studies compare the extent of restenosis at 28 days in an animal model following stent implantation, in bare metal stents, polymer-coated stents, and textured stents.

FIGS. 9A-9F show that both the polymer coated stent and textured stent greatly reduced levels of restenosis. In general, the vessels with polymer drug-coated stent and textured stent treatments appeared to be well-healed with a well established endothelial layer. There is evidence of complete healing and vessel homeostasis at 28 days post implant.

Further trials demonstrate the ability of the stents described herein to limit the extent of restenosis over an extended period of at least three months. The studies are summarized in Example 4, explained in further detail below.

Briefly, the studies compare the extent of restenosis at 3 months following stent implantation with bare metal stents (BMS) and polymer free drug eluting (pfDES) stents. Histomorphometry data shown in Table 4 (below) shows the pfDES greatly reduced levels of restenosis as compared to the BMS.

The following examples illustrate various aspects of the making and using the stent invention herein. They are not intended to limit the scope of the invention.

Example 1

In Vitro Drug Release of Biolimus A9™ from Stents

In vitro drug release was conducted with Biomatrix® II stents coated with a polymer containing the antiproliferative drug Biolimus A9™ and with stents containing an ablumenal microstructure including Biolimus A9™ in a PBS pH 7.4/Tween medium at 37° C. Sampling was periodically conducted and the total amount of Biolimus A9™ was measured by HPLC. FIG. 5, as previously described, illustrates drug release from the Biomatrix® II stent and the microstructure stent.

Example 2

Roughness Factor Bench Test

The outer surface of a Bioflex II 6 crown stent was treated with an abrasive to create a selectively micro-structured outer surface of the stent for drug loading capacity, called Bio-Freedom Stent (FS). The therapeutic agent can be coated directly on the selectively microstructured surface of the stent.

The roughness factor of the FS was characterized using a commercially available Veeco Metrology Group (Tucson, Ariz.) WYKO NT-2000 system, which is a non-contact optical profiler. VSI (vertical scanning interferometer) mode with Vision 32 software, removing cylinder and tilt terms so that the stent surface appears flat. A low pass filter is used which removes the effects of high spatial frequency roughness, smoothing over features that are smaller than a nine pixel window. The results are given in the table below for four different stents whose surface roughness is produced by sand blasting, where Ra is the mean surface roughness, and Rt is the range in surface roughness, as defined above.

|  | Sand Blast 3 in μinches | Sand Blast 4 in μinches | Sand Blast 5 in μinches | Sand Blast 6 in μinches |
|---|---|---|---|---|
| Ra | 30.2 | 25.4 | 25.0 | 28.3 |
| Rt | 688.8 | 336.8 | 406.9 | 358.9 |

Example 3

Animal Implant Tests

Textured stents from Example 2 with and without Biolimus A9™ were implanted in out-bred juvenile swine. A balloon catheter was used to place the stent according to the standard porcine overstretch model with 10-20% overstretch. The juvenile swine target vessels were predilated by known angioplasty techniques prior to stent placement.

After 28 days, the animals were euthanized according to approved protocols, the heart and surrounding tissue was removed from the animals.

Figure 10A:
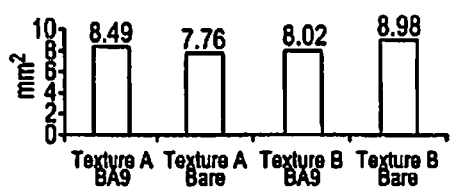
FIGS. 10A-10K are graphs of the histomorphometry of an explanted vessel containing the microstructure stent.
Figure 10B:
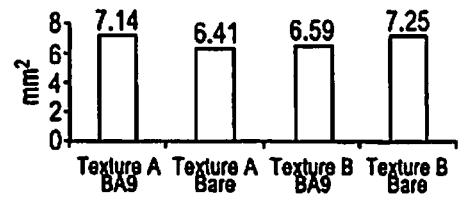
Figure 10C:
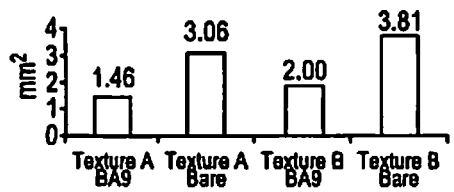
Figure 10D:
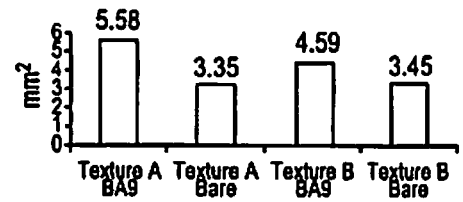
Figure 10E:
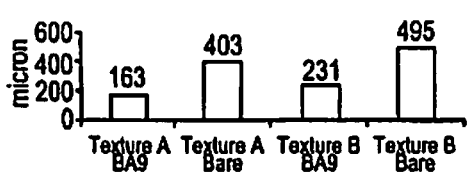
Figure 10F:
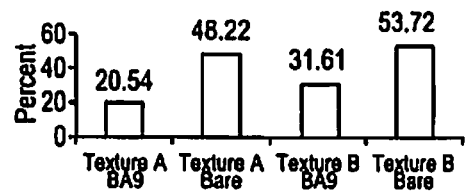
Figure 10G:
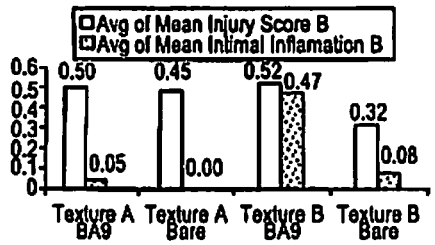
Figure 10H:
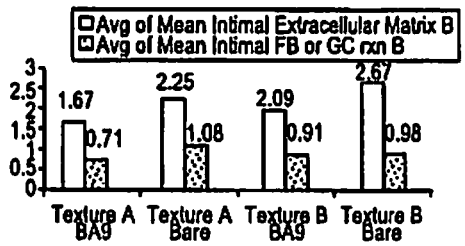
Figure 10I:
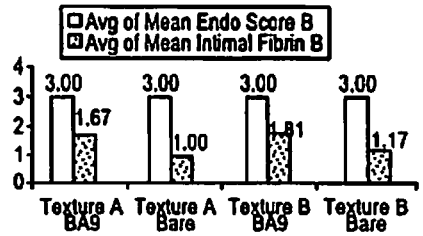
Figure 10J:
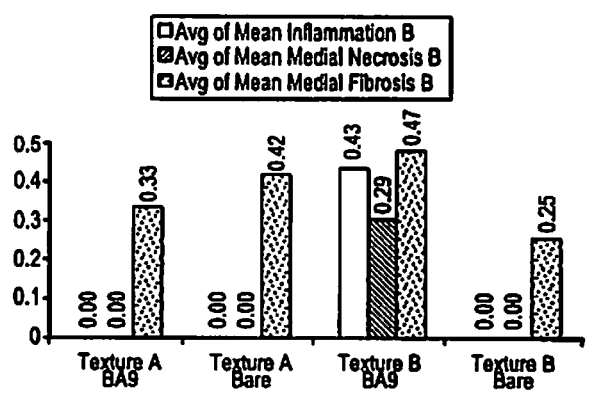
Figure 10K:
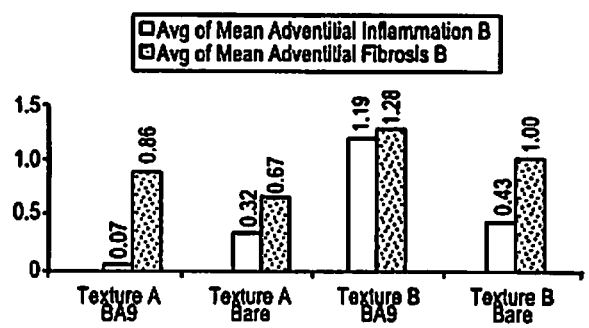

A microscope containing a digital camera was used to generate high resolution images of the vessel cross-sections which had been mounted to slides, with the results shown in FIGS. 9A-9F (previously described). The images were subjected to histomorphometric analysis by the procedure as follows: The stent and artery were dissected, and microtomed by a histologist. The samples were stained for various growth signals, cell proliferation, and other cellular debris. Histomorphometric measurements were made of the artery area in $mm^2$ (FIG. 10A), IEL (FIG. 10B), intimal area in $mm^2$ (FIG. 10C), lumen area in $mm^2$ (FIG. 10D), intimal thickness in microns (FIG. 10E), % area stenosis (FIG. 10F), histologic grading based on injury and inflammation (FIG. 10G), histologic grading based on intimal extracellular matrix and EB/GC reaction (FIG. 10H), histologic grading based on endothelialization and intimal fibrin (FIG. 10I), histologic grading based on medial inflammation, necrosis and fibrosis (FIG. 10J), and histologic grading based on adventitial inflammation and fibrosis (FIG. 10K).

The following table shows the results of the treatment effect at 28 days follow-up. The data in the tables below under column heading "Lumen Area $mm^2$" report the results of morphometric analysis of stents and vessels removed from the pigs at 28 days follow-up (f/u):

TABLE 1

Histomorphometry results

| Stent | Arterial Area $mm^2$ | Lumen/Artery Ratio | Injury Score | Lumen Area $mm^2$ |
|---|---|---|---|---|
| Textured stent without BA9 (textured ablation surface) | 7.76 $mm^2$ | 1.08 | 0.57 | 3.35 ± 0.66 |
| Textured stent with textured ablation surface and 225 μg Biolimus A9 ™ | 8.49 $mm^2$ | 1.08 | 0.50 | 5.68 ± 0.68 |

Figure 8:
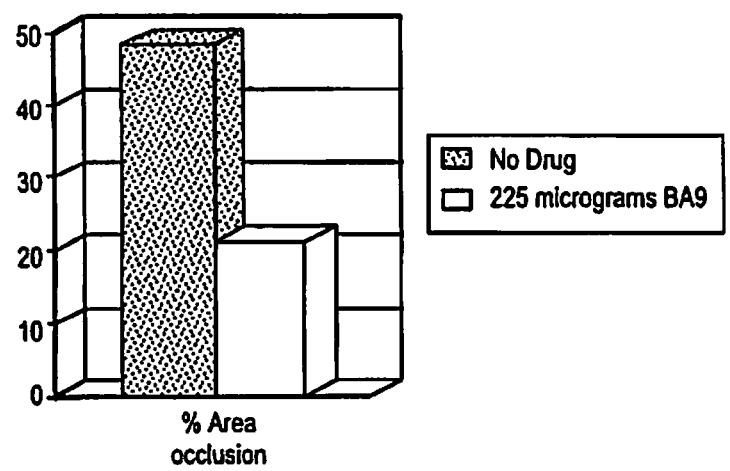
FIG. 8 is a graph showing the percentage of area occlusion for a stent having no drug and a stent having the Biolimus A9™ drug.
Figure 9A:
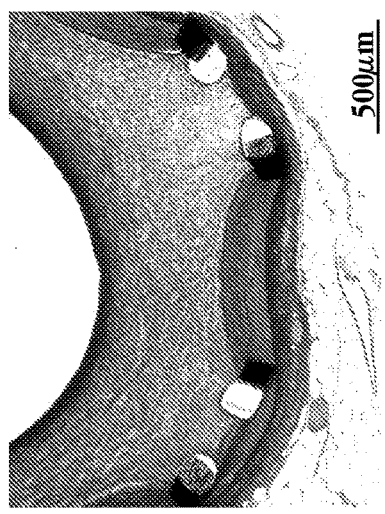
FIGS. 9A-9F are scanned images of histological sections of a vessel 28 days after implantation of a bare-metal stent (FIGS. 9A-9B), a metal-filament stent with a polymer coating containing Biolimus A9™ (FIGS. 9C-9D), and metal-filament microstructure stent with a coating of Biolimus A9™ (FIGS. 9E-9F)
Figure 9C:
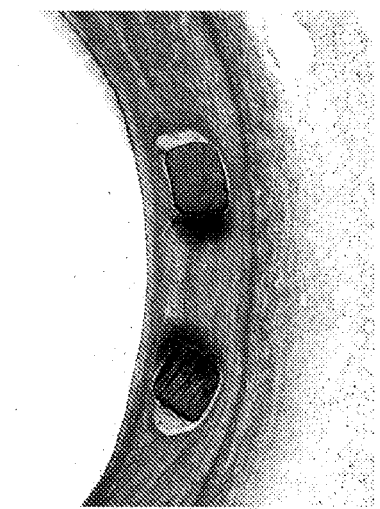
Figure 9E:
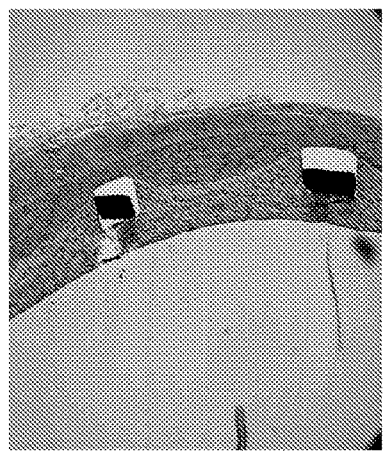
Figure 9B:
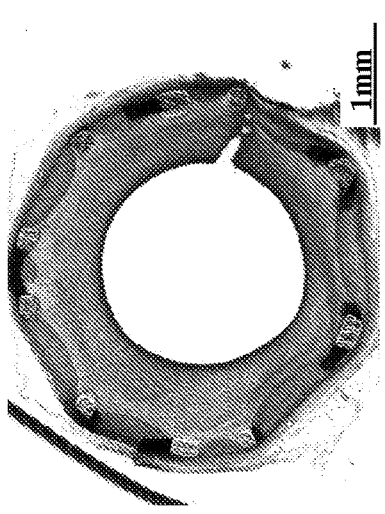
Figure 9D:
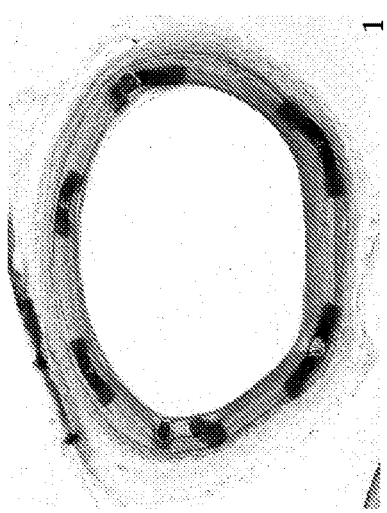
Figure 9F:
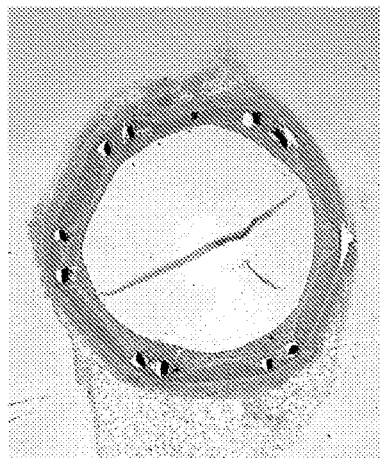

FIG. 8 shows the graph of the % area occlusion for each of the stent with textured surface and the stent with textured surface and 225 μg Biolimus A9™.

Example 4

Three Month Porcine Implant Study

A. Stent Implantation

Polymer Free BioMatrix Stents sandblasted as in Example 2 with 225 μg Biolimus A9™ or a bare BioFlex II stent was implanted in a Crossbred Farm Pig Model according to Table 3.

TABLE 3

Animal Implant Matrix for Porcine Coronary Artery Stents

| | Location/Stent Type | | | |
|---|---|---|---|---|
| Pig No. | LAD | LCX | RCA | Duration |
| 1 | BMS | pf DES | pf DES | Early death |
| 2 | BMS | pf DES | pf DES | 3 months |
| 3 | BMS | n/a* | Pf DES | 3 months |
| 4 | pf DES | pf DES | BMS | 3 months |
| 5 | BMS | pf DES | pf DES | 3 months |

BMS = bare metal stent,
pf DES = polymer free drug eluting stent
*LCX was not stented because of unsuitable size for stenting.

CV Path Institute, Inc. received hearts from 5 pigs. Non-overlapping stenting was performed in 5 pigs, and stents were explanted for light microscopic analysis at three months. Animal 1 died before scheduled follow up at three months for reasons not associated with stent implant procedure at 2 months. The left circumflex coronary artery (LCX) of animal #3 was not stented because the LCX was of an unsuitable size.

B. Materials and Methods: Light Microscopy

For light microscopy, the stented vessel segments were embedded in methylmethacrylate plastic and sections from the proximal, middle, and distal stent were cut, mounted on charged slides, and stained with hematoxylin and eosin and Elastic Van Gieson (EVG). The non-stented proximal and distal sections of the artery were embedded in paraffin, sectioned at four to five microns, and stained with hematoxylin and eosin and EVG. All sections were examined by light microscopy for the presence of inflammation, thrombus, neointimal formation and vessel wall injury.

Morphometric Analysis

Morphometric software (IP Lab for Macintosh, Scanalytics, Rockville, Md.) was calibrated using NIST traceable microscope stage micrometers of 2.0 mm linear and 2.0 mm diameter circle with all objectives. Klarmann Rulings, Inc., (Manchester, N.H.) certified all micrometer graduations. Areas of measurement included the EEL (external elastic lamina), IEL (internal elastic lamina) and lumen. The neointimal thickness was measured at and between stent struts and averaged for each animal. By subtracting IEL from EEL, the medial area was determined. Percent stenosis was derived from the formula [1-(lumen area/stent area)]× 100. Vessel injury score was determined using the Schwartz method (Schwartz R S et al., J Am Coll Cardiol 1992; 19:267-274). Inflammation, fibrin, and injury scores were generated for each section based on a graded analysis of 0=no inflammation/fibrin/injury to value 3=marked Inflammation/fibrin/injury. An inflammation score of 4 was given to sections with 2 or more granulomatous reactions present. Endothelial coverage was semi-quantified and expressed as the percentage of the lumen circumference.

C. Statistical Analysis

The morphometric continuous data were expressed as mean±SD. Statistical analysis of the normally distributed parameters was performed using a Student's t-test. The Wilcoxon test was used in the analysis for non-normally distributed parameters or discrete values. Normality of distribution was tested with the Wilk-Shapiro test. A p value of <0.05 was considered statistically significant.

D. Radiographic Findings

All stents appeared widely and evenly expanded without evidence of fracture or being bent.

E. Light Microscopy Observations

1. Polymer Free DES

All stents were widely expanded and patent without any evidence of thrombus at 3 months after implantation. Neointimal formation was mild with a mean neointimal thickness of 0.16 mm and composed by loosely packed smooth muscle cells and proteoglycan-rich matrix. Vessel injury was mild. Mild fibrin deposition localized around the struts was observed. Although granulomatous response was seen in the LCX of animal #5, inflammation was minimal overall in the other vessels. Giant cells were occasionally observed and documented. Endothelialization was complete without lumenal inflammatory cells and/or platelet adhesion. Notably, a dense calcification was seen in neointima at the proximal section in LCX of animal #2 which contained a bare metal stent.

2. Bare Metal Stents

All stents were widely expanded and patent without any evidence of thrombus at 3 months after implantation. Neointimal formation was mild with a mean neointimal thickness of 0.21 mm and composed of tightly packed smooth muscle cell. Medial rupture was observed in the Left Anterior Descending coronary artery (LAD) of animal #2. This vessel showed severe inflammation mainly around the struts probably due to the injury created by the implant procedure. However, except for this animal, vessel injury and inflammation were mild overall. Fibrin deposition and malapposition were not seen in any stents. Endothelialization was completed without presence of lumenal inflammatory cells and/or platelet adhesion.

F. Histomorphometry

TABLE 4

Morphometric comparison of BMS and polymer free DES at 3 months

| Treatment | Polymer free DES (n = 7) | BMS (n = 4) | p-value |
|---|---|---|---|
| EEL Area (mm$^2$) | 9.52 ± 1.27 | 7.32 ± 0.86 | 0.01 |
| IEL Area (mm$^2$) | 8.16 ± 1.09 | 6.15 ± 0.81 | 0.01 |
| Lumen Area (mm$^2$) | 6.27 ± 1.59 | 4.17 ± 0.98 | 0.04 |

*p-value derived by Wilcoxon test statistical analysis

The results of this animal study demonstrated a significant increase in Lumen Area (i.e. reduction in restenosis) at 3 months after stent implant in a porcine model for the Polymer Free drug eluting stent (Freedom DES) as compared to bare metal control stent implants (BMS).

The description of the invention is merely exemplary in nature and thus, variations that do not depart from the gist of the invention are intended to be within the scope of the invention. Such variations are not to be regarded as a departure from the spirit and scope of the invention.

What is claimed is:

1. A method for making an expandable, metal stent having metal filaments comprising an outer surface region where the outer surface region is coated with a polymer-free limus drug, the stent having a rate of occurrence and/or extent of restenosis or thrombosis resulting from vascular injury in a subject where the rate of occurrence and/or extent of restenosis or thrombosis is reduced relative to that observed by placing at a site of injury, a bare-metal expandable stent formed of interconnected metal filaments or an expandable stent formed of interconnected metal filaments with an outer surface having a coating comprised of a polymer carrier containing a limus drug, the method comprising:

roughening regions of the outer surface of the stent filaments to a surface roughness (Ra) of between 20-40 µin (0.5-1 µm), and a surface roughness range (Rt) of between 300-700 µin (7.5-17.5 µm), and coating the roughened regions of the stent filaments with a polymer-free limus drug, to a coating thickness greater than the Rt of the roughened stent surface.

2. The method according to claim 1, wherein said roughening is carried out by abrading the outer surface region of the stent filaments with a pressurized stream of abrasive particles.

3. The method according to claim 1, wherein said roughening is carried out by forming a hydrocarbon-film mask over regions of the surface of the stent filaments, selectively removing stent material not covered by the mask, and removing the mask.

4. The method according to claim 1, wherein said roughening is carried out by laser etching of the outer surface region of the stent filaments.

5. The method according to claim 1, wherein said roughening is carried out by peening the outer surface region of the filaments to imprint a pattern thereon.

6. The method according to claim 1, wherein said coating is carried out by applying a viscous solution of the drug onto the outer surface region of the stent filament, and drying the solution to form a solid drug coating on the stent filaments.

7. The method according to claim 1, wherein said coating is carried out to apply a final amount of limus drug on the stent of between 80 to 240 µg/cm stent length.

8. The method according to claim 1, wherein the limus drug is 42-O-ethoxyethyl rapamycin.

9. The method according to claim 8, wherein said coating is carried out to produce a final drug coating having a thickness between 5 and 15 μm.

\* \* \* \* \*